US010172576B2

(12) United States Patent
Shealy

(10) Patent No.: US 10,172,576 B2
(45) Date of Patent: Jan. 8, 2019

(54) RADIATION SHIELD FOR X-RAY EXAMINATION TABLE

(71) Applicant: PlastiCraftsmen LLC, Roebuck, SC (US)

(72) Inventor: Andrew Shealy, Roebuck, SC (US)

(73) Assignee: PLASTICRAFTSMEN LLC, Roebuck, SC (US)

( * ) Notice: Subject to any disclaimer, the term of this patent is extended or adjusted under 35 U.S.C. 154(b) by 0 days.

(21) Appl. No.: 15/751,576

(22) PCT Filed: Jun. 16, 2017

(86) PCT No.: PCT/US2017/037838
§ 371 (c)(1),
(2) Date: Feb. 9, 2018

(87) PCT Pub. No.: WO2017/218871
PCT Pub. Date: Dec. 21, 2017

(65) Prior Publication Data
US 2018/0235555 A1   Aug. 23, 2018

Related U.S. Application Data

(60) Provisional application No. 62/351,395, filed on Jun. 17, 2016.

(51) Int. Cl.
A61B 6/10   (2006.01)
A61B 6/00   (2006.01)
(Continued)

(52) U.S. Cl.
CPC ............ *A61B 6/107* (2013.01); *A61B 6/00* (2013.01); *A61B 6/10* (2013.01); *A61B 6/44* (2013.01); *G21F 3/00* (2013.01); *G21F 7/03* (2013.01)

(58) Field of Classification Search
CPC .. A61B 6/107; A61B 6/10; A61B 6/44; G21F 7/03
See application file for complete search history.

(56) References Cited

U.S. PATENT DOCUMENTS 3,967,128 A   6/1976   Smulewicz
3,984,696 A   10/1976   Collica et al.
(Continued)

FOREIGN PATENT DOCUMENTS

CN   2011/31752 Y    10/2008
GB   2011/2472246 A1  2/2011
(Continued)

OTHER PUBLICATIONS

Bertrand, Olivier et al. "Best Practices for Transradial Approach in Diagnostic Angiography and Intervention," Wolters Kluwer Health, pp. 272-273 (2015).
(Continued)

*Primary Examiner* — Nicole M Ippolito
*Assistant Examiner* — Sean M Luck
(74) *Attorney, Agent, or Firm* — Thrive IP; Bernard Klosowski

(57) ABSTRACT

Radiation shield assemblies for attenuation of X-ray radiation between a patient and attending medical staff are attachable to an examination table for monitoring the patient during X-ray examination procedures.

27 Claims, 19 Drawing Sheets

(51) Int. Cl.
  *G21F 7/03* (2006.01)
  *G21F 3/00* (2006.01)

(56) References Cited

U.S. PATENT DOCUMENTS

| | | | |
|---|---|---|---|
| 4,255,667 | A | 3/1981 | Bolin et al. |
| 4,662,366 | A | 5/1987 | Tari |
| 4,742,981 | A | 5/1988 | Converse |
| 4,893,323 | A | 1/1990 | Cook, III |
| 4,923,162 | A | 5/1990 | Fleming et al. |
| 4,957,120 | A | 9/1990 | Grier-Idris |
| 4,970,900 | A | 11/1990 | Shepherd et al. |
| 5,006,718 | A | 4/1991 | Lenhart |
| 5,742,962 | A | 4/1998 | Yoshino et al. |
| 6,101,650 | A | 8/2000 | Omdal et al. |
| 6,467,487 | B1 | 10/2002 | Rios |
| 6,481,888 | B1 | 11/2002 | Morgan |
| 6,674,087 | B2 | 1/2004 | Cadwalader et al. |
| 6,895,618 | B2 | 5/2005 | Jahrling |
| 7,103,932 | B1 | 9/2006 | Kandora |
| 7,591,590 | B2 | 9/2009 | Cadwalader et al. |
| 7,663,128 | B2 | 2/2010 | Arterson |
| 8,369,933 | B2 | 2/2013 | Crisco et al. |
| 8,700,131 | B2 | 4/2014 | Goff et al. |
| 2003/0167569 | A1 | 9/2003 | Newkirk et al. |
| 2004/0186547 | A1 | 9/2004 | Dorn et al. |
| 2005/0235421 | A1 | 10/2005 | Ansel |
| 2009/0122020 | A1* | 5/2009 | Eliasson ............... G06F 3/0421 345/173 |
| 2011/0184278 | A1 | 7/2011 | Goff et al. |
| 2013/0072787 | A1* | 3/2013 | Wallace .................. A61B 6/12 600/424 |
| 2013/0292521 | A1 | 7/2013 | Chepurny |
| 2016/0038365 | A1 | 2/2016 | Conner et al. |
| 2017/0265824 | A1 | 9/2017 | Wasson, Jr. et al. |

FOREIGN PATENT DOCUMENTS

| | | |
|---|---|---|
| WO | 2002/015198 A1 | 2/2002 |
| WO | 2012/121765 A1 | 9/2012 |
| WO | 2013/089608 A1 | 6/2013 |
| WO | 2014/028233 A1 | 2/2014 |
| WO | 2015/012906 A1 | 1/2015 |

OTHER PUBLICATIONS

Screen shot of radiation barrier by MarShield, accessed Jun. 15, 2017, from https://marshield.com/medical-shielding/shields-barriers-booths-rooms/radiation-shielding-barriers/.
Screen shot of radiation barrier by AliMed, accessed Jun. 15, 2017, from https://www.alimed.com/rayshield-frame-mounted-overhead-lead-acrylic-barriers.html?atrkid=V3ADWA342718F_20842379404_pla-124953471604_66599238484_g_c_pla_with_promotion_1o6&gclid=CNKE447Iv9QCFQltaQod8yUPLg.
Screen shot of radiation barrier by Supertech, accessed Jan. 30, 2018, from https://www.supertechx-ray.com/ApronsandBarriers/LeadPlasticBarriers/AdjustableHeightMobileBarriers.php.
Screen shot of radiation barrier by Kenex, accessed Jan. 30, 2018, from http://kenex.co.uk/products/x-ray-shielding/mobile-shields/height-adjustable-over-table-shield-model-32605.
Screen shot of radiation barrier by Supertech, accessed Jan. 30, 2018, from https://www.supertechx-ray.com/ApronsandBarriers/LeadPlasticBarriers/Rayshield-S-620.php.
Screen shot of radiation barrier by Supertech, accessed Jan. 30, 2018, from https://www.supertechx-ray.com/ApronsandBarriers/LeadPlasticBarriers/SideRailMountedBarriers.php.
Screen shot of radiation barrier by Direct Scientific, accessed Jan. 30, 2018, from https://www.drct.com/dss/shielding/lead_glass_shield.htm.

* cited by examiner

RADIATION SHIELD FOR X-RAY EXAMINATION TABLE

CROSS-REFERENCE TO RELATED APPLICATIONS

This application claims benefit of U.S. Provisional Patent Application Ser. No. 62/351,395, filed in the United States Patent and Trademark Office on Jun. 17, 2016, which is incorporated herein by reference in its entirety.

BACKGROUND

An X-ray technician or other attending medical personnel may need to be positioned near a patient during an X-ray examination in order to conduct certain ancillary procedures or to hold the patient's limb or a small child or infant in position during the examination. Accordingly, the technician can be exposed to excess radiation, particularly over the course of time and multiple procedures. Aside from the potentially adverse impact of overexposure to radiation on the health of the technician, government regulations limit worker exposure to radiation. Thus, unnecessary exposure to radiation can result in premature removal of experienced staff from X-ray examination rooms where they are most needed.

Conventional rollaway radiation screens positioned between medical personnel and an examination table not only block medical personnel from reaching the patient but may prevent staff from seeing the patient unless the staff steps around the screen to adjust the patient or to conduct a procedure. This defeats the purpose of the conventional screen during an X-ray examination.

Moreover, equipment clutter in an examination room can become problematic, especially during emergency procedures. Equipment that gets in the way of staff during emergency situations is often pushed out of the way, even equipment intended for staff safety. Also, due to its continual repositioning, the necessary equipment is rarely in proper position when needed, so it often goes unused.

What is needed in the medical field is a system that reduces or eliminates staff exposure to radiation during X-ray examinations without impairing the ability of medical personnel to physically reach the patient to obtain the necessary medical images during an X-ray. The desired system also should be economical to manufacture, and it should be simple, effective, and reliable to use and reuse.

BRIEF SUMMARY OF THE DISCLOSURE

The present disclosure is directed in general to shields that block or reduce X-ray radiation from medical personnel who are in proximity to a patient undergoing an X-ray examination. More specifically, the shields permit medical personnel to work near a patient undergoing an X-ray, up to and including physical contact with the patient. As will be understood from the present disclosure and by its practice, the various embodiments described herein and their equivalents are simple to manufacture, install and use.

For example, in one embodiment according to the present disclosure, a radiation shield assembly may include a radiation attenuating screen being at least partially transparent; a base attachable substantially parallel to a surface of an examination table, the radiation attenuating screen connectable to the base to interpose the radiation attenuating screen between attending medical staff and a patient disposed on the examination table, the partially transparent radiation attenuating screen configured to permit the medical staff to manipulate control icons on the radiation attenuating screen while simultaneously viewing the patient therethrough; wherein the radiation attenuating screen depends at an angle from the base in a direction of the surface of the examination table to permit the medical staff to incline in a direction of the patient, the radiation attenuating screen including a radiodense material to reduce radiation exposure to the medical staff while irradiating the patient. The radiation attenuated while irradiating the patient may be measured in milliroentgens per hour (mR/hr)

In this embodiment the radiation attenuating screen may be a lead (Pb) acrylic sheet from about 10 mm to about 14 mm in thickness, more particularly about 12 mm. The radiation attenuating screen may include a touch screen and the control icons may include an on-control, an off-control, a camera record control, a zoom control, and/or a voice control.

The radiation attenuating screen may reduce radiation exposure to facial areas of attending medical staff from about ninety percent to about ninety-four percent, more particularly by about ninety-three point eight percent (93.8%), and may reduce radiation exposure to abdominal areas of attending medical staff from about ninety-five percent to about ninety-nine percent, more particularly by about ninety-seven point four percent (97.4%).

The angle of the radiation attenuating screen in this example may be about twenty-five degrees as measured from the vertical, or perpendicular or orthogonal to level ground. More particularly, the angle of the radiation attenuating screen may be adjustable from about five degrees to about forty-five degrees measured from vertical.

The radiation shield assembly in this embodiment may also include a frame disposed about the radiation attenuating screen. The frame is configured at about twenty-five degrees from vertical to cause the radiation attenuating screen to depend from the base at the angle in the direction of the surface of the examination table. The base may include a plurality of apertures therein and the frame may include a plurality of tabs depending therefrom. The tabs may be configured to slot into the apertures to seat the base and the frame together. In one aspect, there may be more apertures than tabs such that the tabs can be seated in different apertures to move the radiation attenuating screen relative to the examination table.

Also in this embodiment, the frame may further include a latch retractor and a latch, and the base may have a notch to receive the latch with the latch being controllable by the latch retractor to release the latch from the notch. The radiation shield assembly can also include an attachment assembly connectable to the examination table with the base being connectable to the attachment assembly.

In another embodiment, a radiation shield assembly may include a radiation attenuating shield having a plurality of tabs depending therefrom; a base attachable substantially parallel to a surface of an examination table, the base having a plurality of apertures therein for receiving the tabs of the radiation attenuating shield to interpose the radiation attenuating shield between attending medical staff and a patient disposed on the examination table, the radiation attenuating shield depending at an angle from the base in a direction of the surface of the examination table to permit the medical staff to incline in a direction of the patient, the radiation attenuating shield including a radiodense material to reduce radiation exposure to the medical staff while irradiating the patient.

In this embodiment, the radiation attenuating shield may have a top, a bottom, a first side and a second side, with at least two of the tabs extending from the top and at least two tabs extending from the bottom. One or more sets of the tabs at the top and the bottom can be angled, bent or inclined to cause the radiation shield assembly to angle toward the table. Additionally, or alternatively, the radiation shield assembly can be formed with a bend to cause the radiation shield assembly to angle toward the table from about five degrees to about forty-five degrees from vertical, more particularly about twenty-five degrees from vertical in a direction of the examination table. The bend can be set off from center and the radiation shield assembly can have a first portion depending from the bend that is longer than a second portion depending from the bend.

In this example, the radiodense material is equivalent to about 0.5 mm lead such that the radiation attenuating screen reduces radiation exposure to attending medical staff from about ninety percent to about ninety-nine percent.

In a further embodiment, a radiation shield assembly may include a frame having a top, a bottom, a first side and a second side, a plurality of tabs depending from one of the top, bottom, first side or second side; a radiation attenuating screen disposed within the frame, the radiation attenuating screen being transparent and including a radiodense material to reduce radiation exposure to attending medical staff during a procedure; a base attachable substantially parallel to a surface of an examination table, the tabs of the frame connectable to the base to interpose the radiation attenuating screen between the attending medical staff and a patient disposed on the examination table, the transparent radiation attenuating screen configured to permit the medical staff to view the patient during the procedure; wherein the tabs or the frame depend at an angle in a direction of the surface of the examination table to permit the medical staff to incline in a direction of the patient.

The radiation attenuating screen in this embodiment may include a lead (Pb) acrylic sheet from about 10 mm to about 14 mm in thickness, more particularly about 12 mm such that radiation exposure to attending medical staff is reduced from about ninety percent to about ninety-nine percent.

The radiation shield assembly may also include controls connected to one of the frame or the base. The controls may include one or more of an on-control, an off-control, a camera record control, a zoom control, a voice control and the like. In a further aspect, a camera is included and attachable to the frame, and a portion of the radiation attenuating screen is a video monitor in communication with the camera for monitoring the patient.

The angle of the radiation attenuating screen in this embodiment may be adjustable from about five degrees to about forty-five degrees from vertical, more particularly about twenty-five degrees from vertical in a direction of the examination table.

Additional aspects of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the disclosure without departing from the spirit and scope of the subject matter. Variations may include, but are not limited to, substitution of equivalent means, features, or steps for those illustrated, referenced, or discussed, and the functional, operational, or positional reversal of various parts, features, steps, or the like. Those of ordinary skill in the art will better appreciate the features and aspects of such variations upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION OF THE DISCLOSURE

Figure 1:
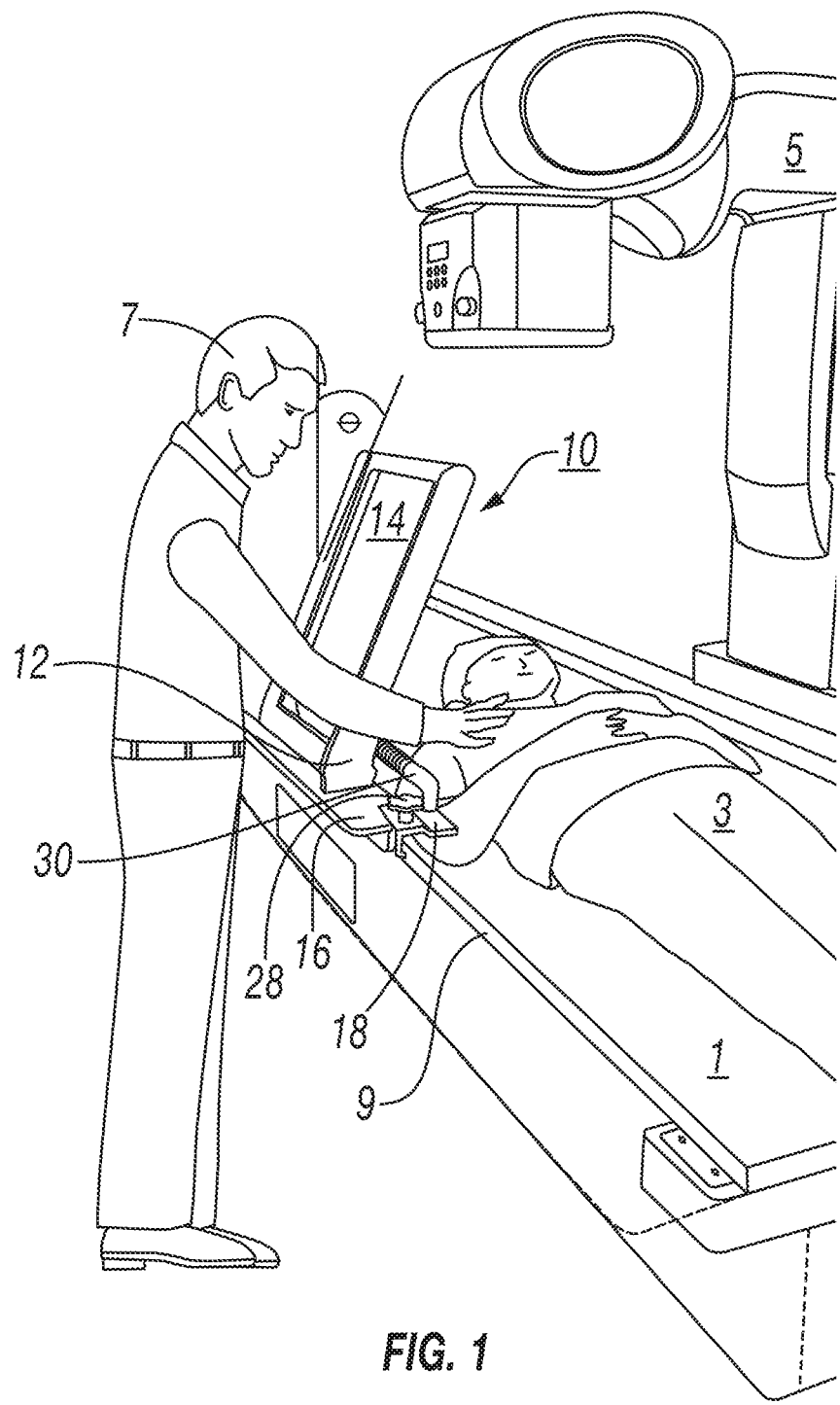
FIG. 1 is a perspective view of a radiation attenuating viewing shield in an intended use environment according to an aspect of the disclosure.

Detailed reference will now be made to the drawings in which examples embodying the present subject matter are shown. The detailed description uses numerical and letter designations to refer to features of the drawings.

The drawings and detailed description provide a full and written description of the present subject matter, and of the manner and process of making and using various exemplary embodiments, so as to enable one skilled in the pertinent art to make and use them, as well as the best mode of carrying out the exemplary embodiments. However, the examples set forth in the drawings and in the detailed description are provided by way of explanation only and are not meant as limitations of the disclosure. The present subject matter thus includes any modifications and variations of the following examples as come within the scope of the appended claims and their equivalents.

Turning now to FIG. 1, a radiation shield assembly for attenuation of X-radiation is designated in general by the number 10. The shield assembly 10 is structured in general for adjustable attachment to an X-Ray examination table 1 and for placement between a patient 3 and an X-ray technician 7 or other attending personnel. As will be explained in greater detail below, the shield assembly 10—by blocking or reducing radiation emitting from an X-Ray device 5—permits the technologist 7 to remain in the examination room during an X-Ray procedure while also allowing physical access to the patient 3. For instance, medical personnel 7 may be required to attend to the patient 3 during an X-Ray examination if the patient 3 requires pain management or while the patient 3 swallows barium or undergoes fluoroscopy, back up specials, cystoscopy, and the like.

The system 10 shown in FIG. 1 broadly includes a holder or frame 12, a radio-dense viewing shield or screen 14, and a base or platform 16. The frame 12 attaches to the base 16, which in turn attaches to a connection or attachment device 18 using screws, clamps, heat welding, snaps, rivets, and the like. The table connection device 18 utilizes, for example, a connector 28 such as a screw-in handle or knob that can be loosened or tightened to attach, adjust, or detach the attachment device 18 from the table 1. Here, the attachment device 18 attaches to an edge 9 of the examination table 1 and may also include a handle or grip 30 that can be used to transport or adjust the attachment device 18, or the patient 3 can grip it for support as well. The Shimadzu company provides a suitable table connection device that can be employed as the attachment device 18, although the disclosure is not limited to this example.

Also shown in FIG. 1, the frame 12 as well as the platform 16 may be made from durable, water-resistant, reusable materials such as high-density polyethylene (HDPE). In this example, the frame 12 is formed at an angle θ depending from the platform 16. More specifically, the angle θ of the frame 12 and the viewing screen 14 is about twenty-five degrees measured from vertical (025°). This permits the X-ray technician 7 to lean in and reach around the frame 12 as shown in FIG. 1 in order to access and adjust the patient 3 or to perform a procedure on the patient 3 while the X-Ray device 5 is irradiating the patient 3. In some embodiments, the angle θ of the frame 12 is formed, or adjustable, from about five degrees (5°) to about forty-five degrees (45°) from vertical (orthogonal to level ground); thus, the disclosure is not limited to the example shown.

With more particular reference to the radio-dense viewing screen 14 of FIG. 1, the screen 14 is at least partially see-through or clear or fully transparent to allow the technologist 7 or attending physician to view the patient 3 through the screen 14 while simultaneously working on the patient 3. The exemplary shield 14 is an acrylic, lead-impregnated sheet approximately 12 millimeters (mm) in thickness. The radio-dense acrylic screen 14 provides equivalent protection of a 0.5 mm thick lead (Pb) sheet. By way of further example, the acrylic screen 14 may range from about 8 mm in thickness (0.25 mm Pb equivalent) to about 24 mm in thickness (1 mm Pb equivalent).

Figure 2:
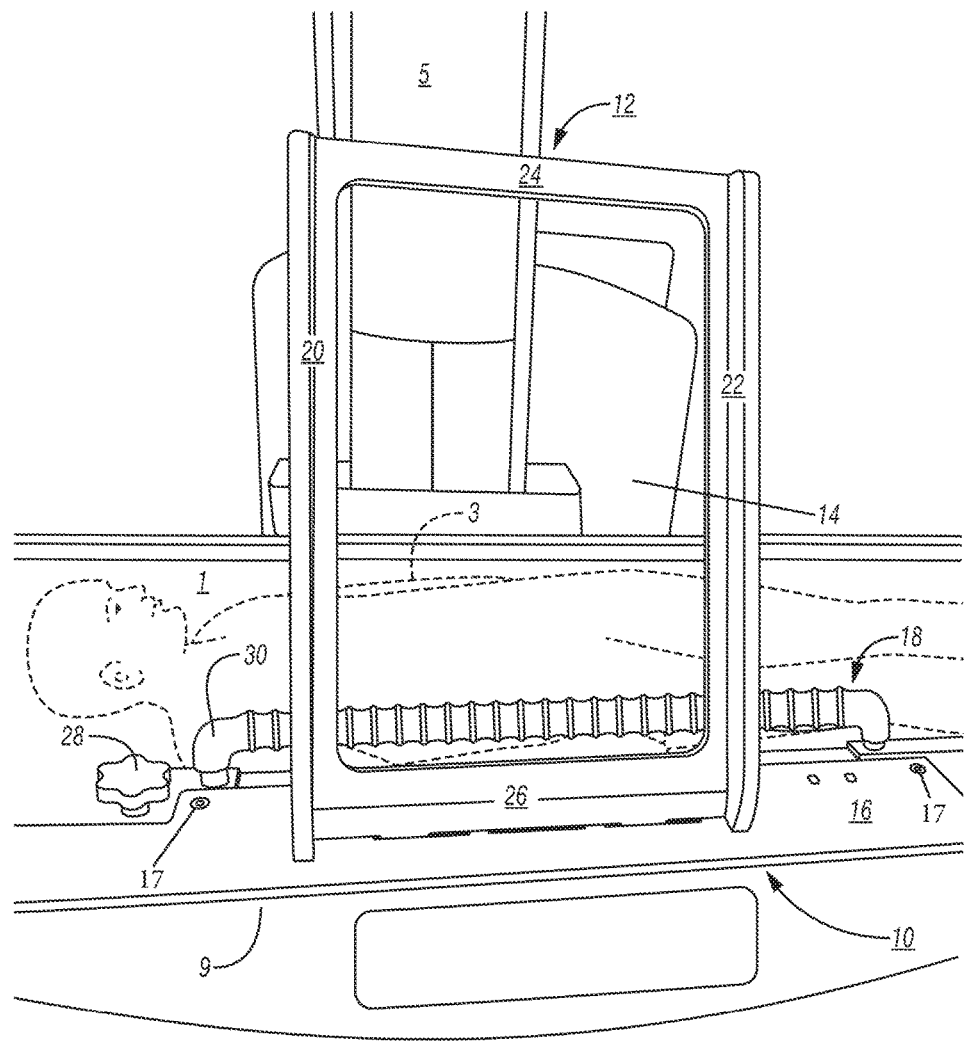
FIG. 2 is a front elevational view of the shield as in FIG. 1.

FIG. 2 most clearly shows the radiation shield assembly 10. The patient 3 is on the table 1 and can be seen through the viewing shield 14. Here again, the radio-dense viewing shield 14 is supported within the frame 12, which as briefly introduced, is releasably attached to the base 16 that is in turn releasably connected to the attachment device 18. The device 18 (including its handle 30) is also releasably connected to a portion 9 of the examination table 1 using knob 28 or screws, snaps, and the like (not shown).

More specifically, the frame 12 of FIG. 2 includes a first wall or side 20, a second wall or side 22, a first edge or top 24, and a second edge or bottom 26, which hold the viewing shield 14 therebetween. Although the shield 14 can be made to stand on its own, the durable frame 12 not only provides the desired angle θ noted above, but the frame 12 serves to protect the acrylic screen 14 from peripheral contact and damage. Notably, a portion of the X-Ray 5 can be seen through the acrylic screen 14, which protects medical personnel standing in the foreground of FIG. 2 from radiation being emitted from the X-Ray machine 5.

Figure 3:
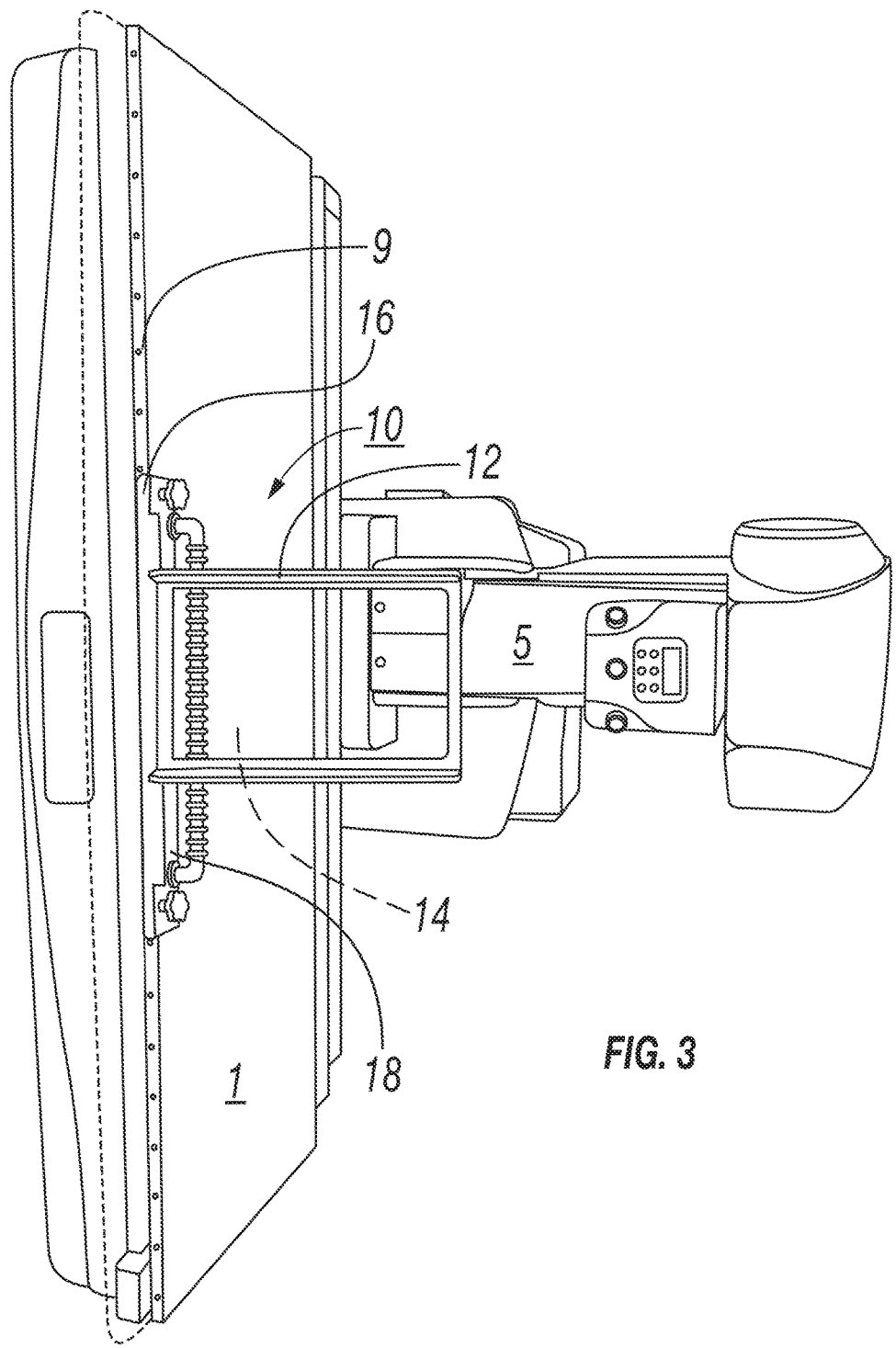
FIG. 3 is another perspective view of the shield as in FIG. 1, particularly showing an alternative orientation according to another aspect of the disclosure.

FIG. 3 shows the radiation shield assembly 10 in another configuration. Here, the table 1 has been adjusted vertically for a patient to stand, for instance, for an X-ray examination using the X-Ray machine 5. As introduced and shown again in FIG. 3, the assembly 10 may include the frame 12, the transparent shield 14, the base 16, and the attachment device 18, which is connected to the table edge 9. As will be described with respect to FIG. 4 below, connection components of the shield assembly 10 permit it to extend at ninety degrees as shown in FIG. 3 without the shield assembly 10 slipping or falling away from the table 1.

Figure 4:
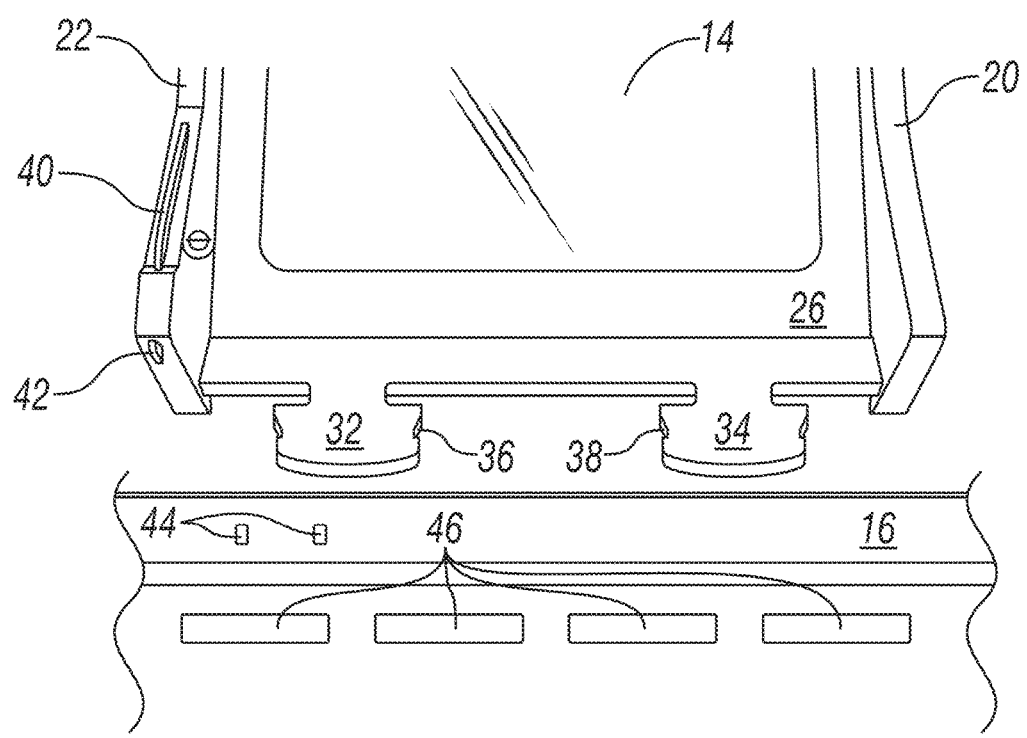
FIG. 4 is a partial, cutaway, exploded, rear elevational view of the shield as in FIG. 2.

In FIG. 4 connection components of the shield assembly 10 may include one or more appendages or projections such as tabs 32, 34 that may extend from a portion of the frame 12 such as its bottom 26. An angle θ may be formed by bending or inclining the bottom 26 and/or its tabs 32, 34 relative to the walls 20, 22. Here, the wall 22 also includes a release, latch retractor, or trigger 40 that controls a spring-loaded projection, protuberance, pin or finger 42. By way of example, to mate the frame 12 with the base 16, the tabs 32, 34 with respective indentations 36, 38 are extended through respective apertures or slots 46 in the base 16. As shown, multiple slots 46 may be provided to adjust the frame 12 along the base 16 to accommodate different patient sizes, table and patient positions, et cetera. Additionally, the spring-loaded projection 42 recesses upon contact with a surface of the base 16 until it is aligned with one of various slots 44 in the base 16. Once the projection 42 aligns with a slot 44, the projection 42 springs into that slot 44 and renders the frame 12 stationary relative to the base 16. Moreover, when the base 16 is connected to the attachment device 18, the T-shaped tabs 32, 34 and their indentations 36, 38 cooperate with the attachment device 18 to help render the frame 12 stationary; i.e. to lock the frame 12 in place to the left and to the right.

Figure 5:
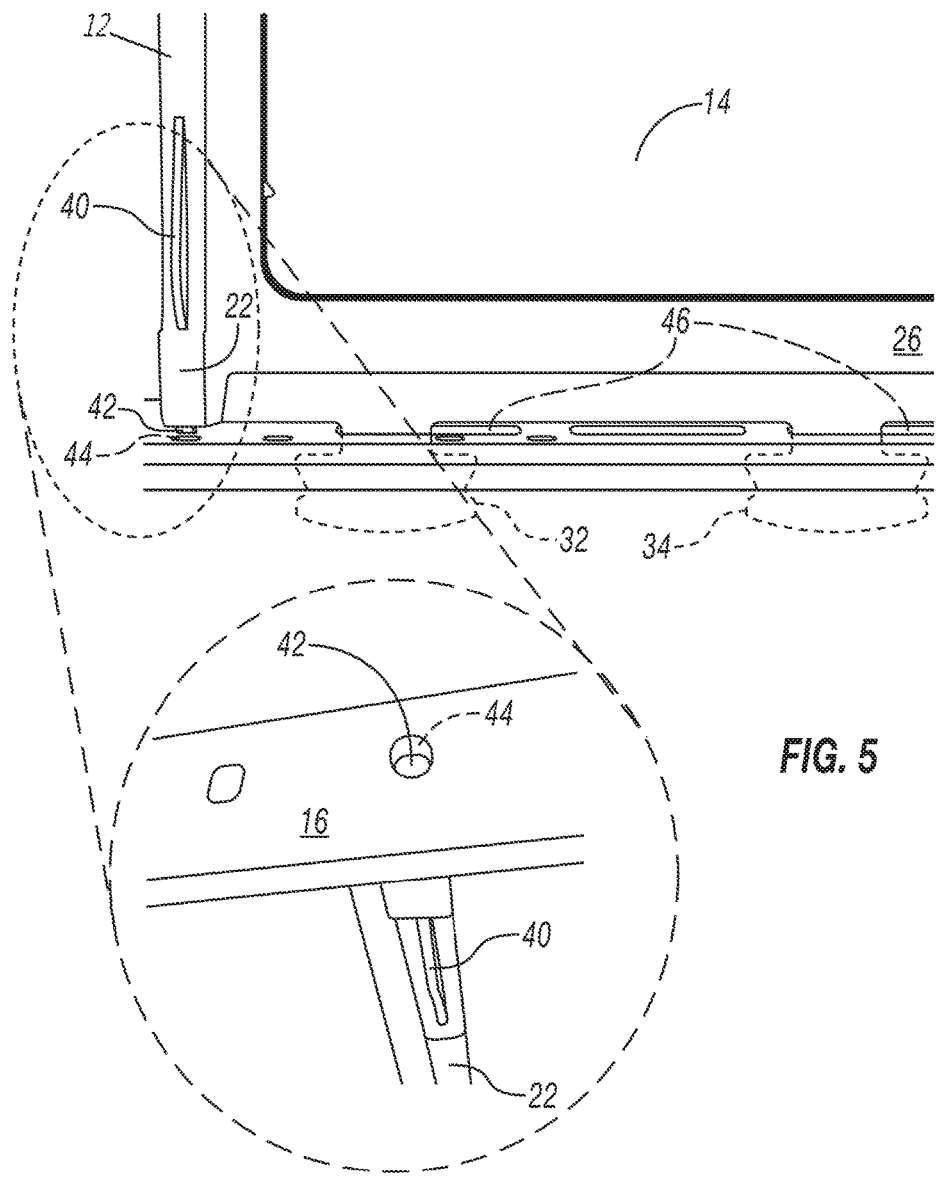
FIG. 5 is a partial, cutaway, rear elevational view of the shield as in FIG. 4, particularly showing exemplary connection aspects in phantom for clarity and in inset.

Turning to FIG. 5, the tabs 32, 34 are shown in phantom extending through respective apertures 46 in the base 16. The spring-loaded pin 42 extending from wall 22 is shown poised above one of the slots 44. As shown in the enlarged inset (from a bottom perspective for clarity), the pin 42 has extended into the slot 44 to lock the frame 12 relative to the base 16. When release is desired, the latch retractor 40 can be pulled or depressed to retract the latch 42 from the slot 44. Suitable material for latch retractor 40 and latch 42 are made of Delrin™ material. Delrin™ material is a very dense, wear resistant plastic. Moreover, the Delrin™ made parts may be formed with a different color than the rest of the frame 12 so that the latch retractor 40 and the latch 42 can be easily seen and located quickly. Thus, medical personnel can verify at a glance that the latch 42, for instance, is projecting into the slot 44 before a procedure, particularly if the table is to be rotated.

Figure 6:
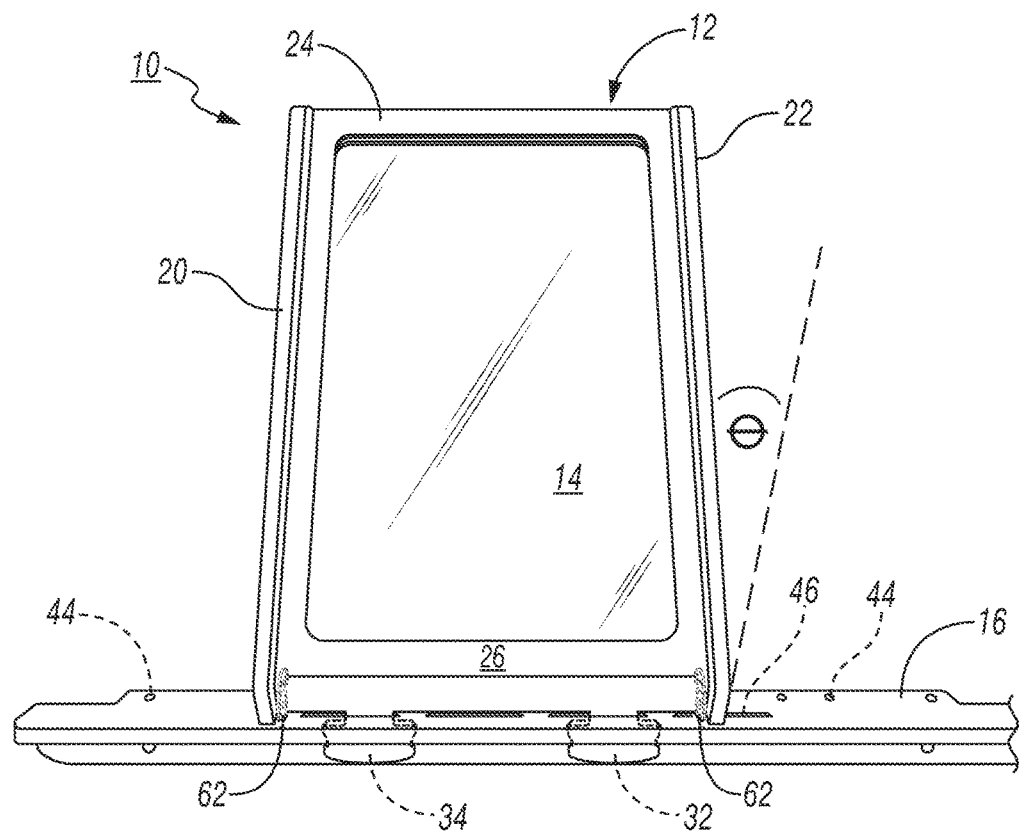
FIG. 6 is a front elevational view of the shield as in FIG. 1, particularly showing an exemplary angular aspect partially in phantom for clarity.

FIG. 6 most clearly shows the frame 12 disposed at angle θ relative to the base 16 with the first side 20, the second side 22, the top 24, and the bottom 26 surrounding the radio-dense viewing shield 14. Here, an optional adjustment mechanism 62 such as a ratchet and pawl may be included for adjusting the assembly 10 to the desired angle θ. As further shown, the spring-loaded projection 42 (see inset FIG. 5) is aligned with and extending through one of the slots 44 in the base 16. Likewise, the tabs 32, 34 (in phantom) extend through respective apertures 46.

Figure 7:
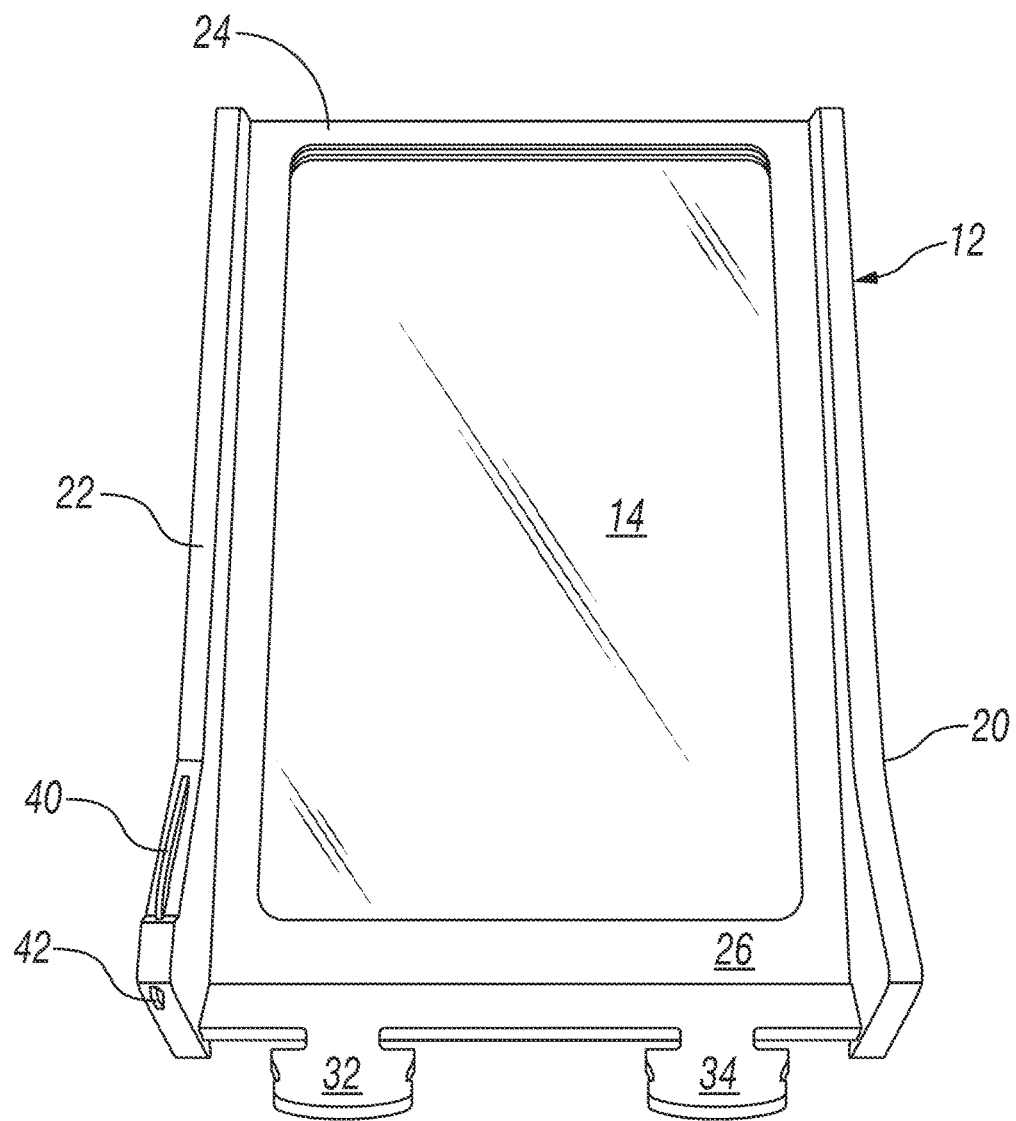
FIG. 7 is a rear elevational view of the shield as in FIG. 1.

FIG. 7 most clearly shows the frame 12 with the first side 20, the second side 22, the top 24, and the bottom 26 surrounding the radio-dense viewing shield 14. The spring-loaded projection 42 and its control release 40 as well as the tabs 32, 34 are also clearly shown in FIG. 7.

Figure 8:
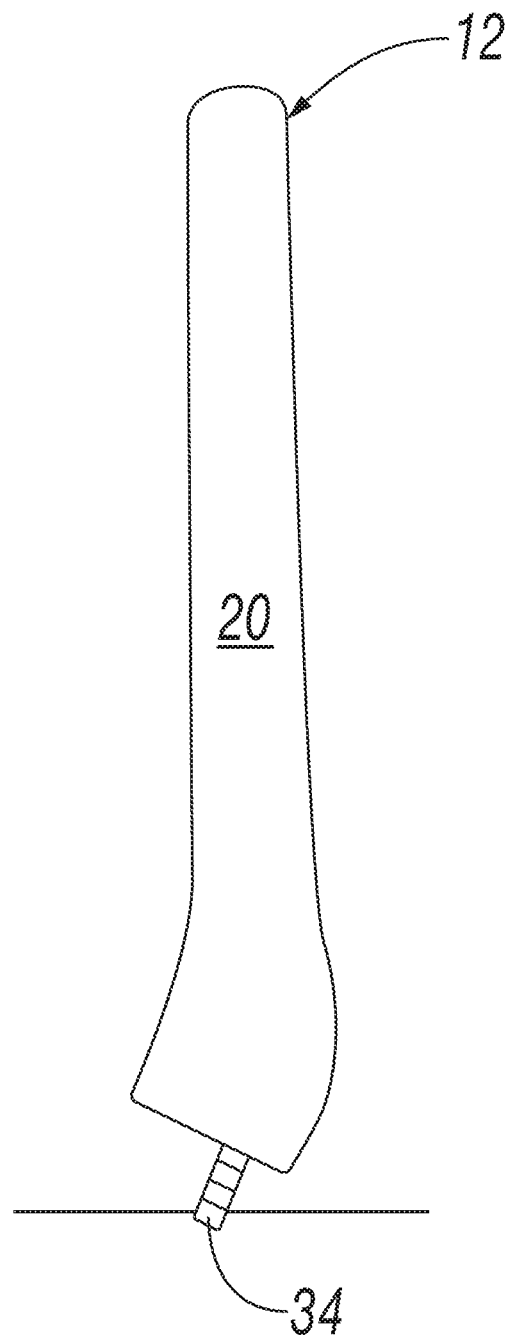
FIG. 8 is a first side view of the shield as in FIGS. 1 and 2.
Figure 9:
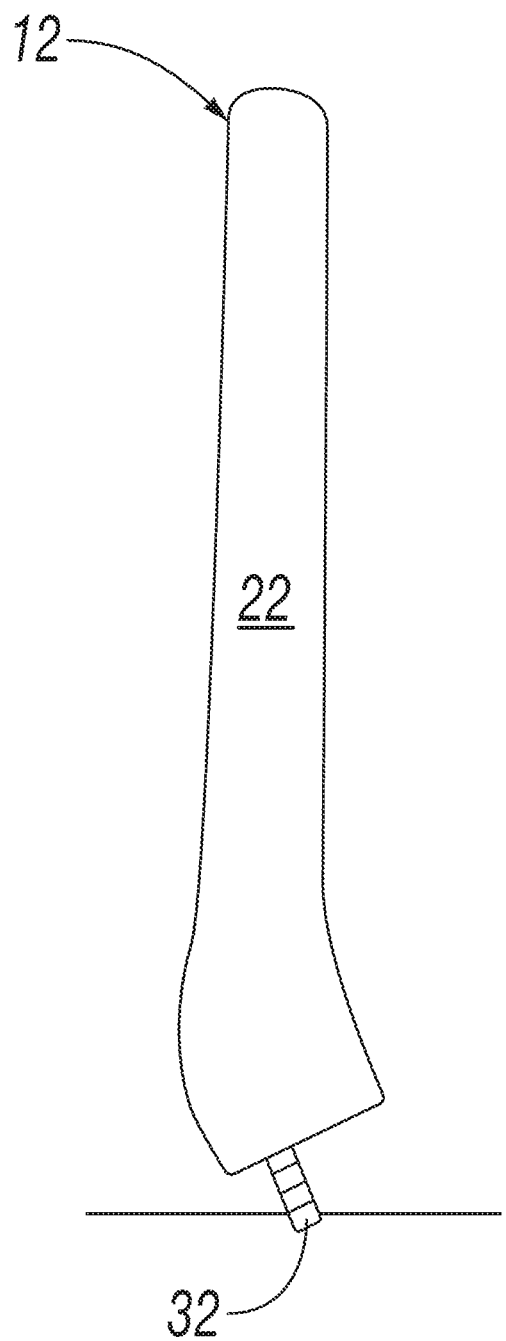
FIG. 9 is a second side view of the shield as in FIGS. 1 and 2.

With reference to FIG. 8, a view of the left side 20 of the frame 12 shows the tab 34 extending therefrom. Similarly, FIG. 9 shows the right side 22 of the frame 12 with the tab 32 extending therefrom.

Figure 10:
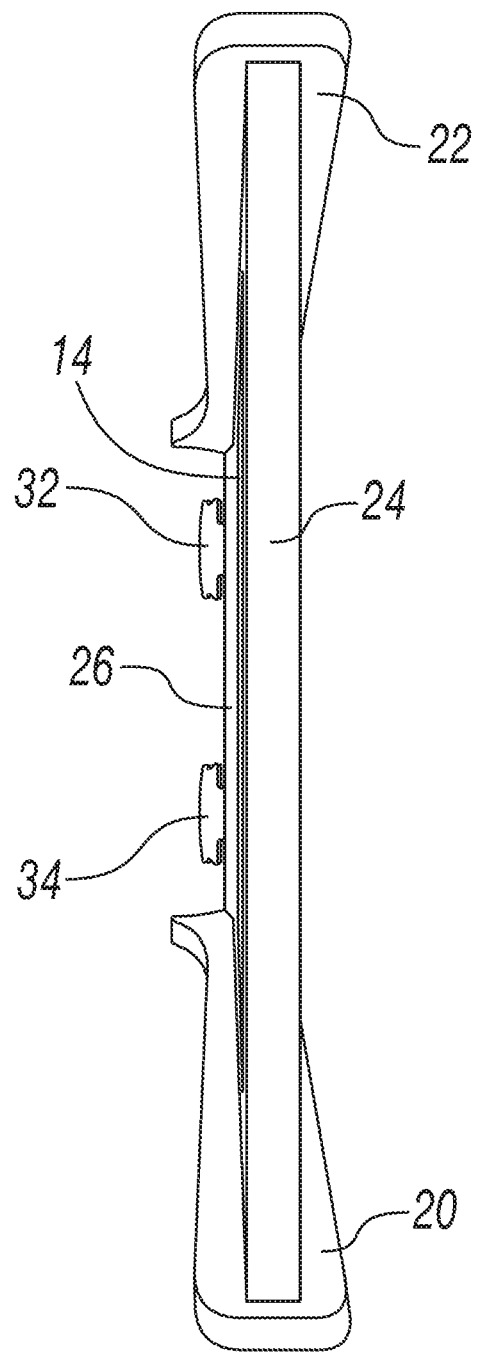
FIG. 10 is a top end view of the shield as in FIGS. 1 and 2.

FIG. 10 shows the top side 24 of the frame 12 most clearly with the tabs 32, 34 extending at an angle from the bottom 26. Also partially shown is the screen 14.

Figure 11:
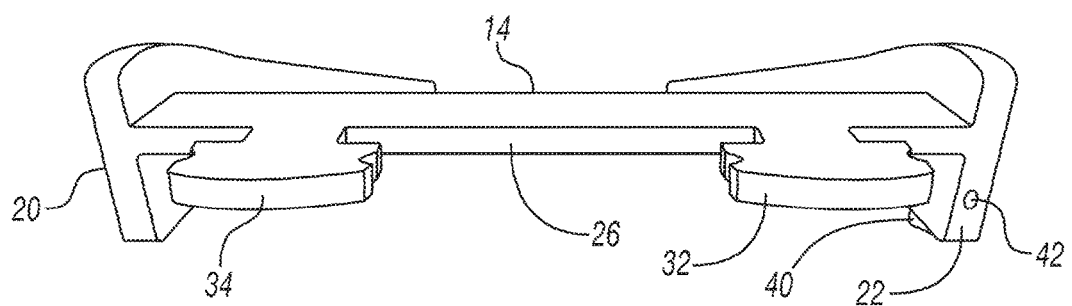
FIG. 11 is a bottom end view of the shield as in FIGS. 1 and 2.

FIG. 11 shows the bottom 26 with the tabs 32, 34 extending therefrom with the screen 14 in the background. Here also, the trigger 40 and catch 42 can be seen extending from the wall 22.

Figure 12:
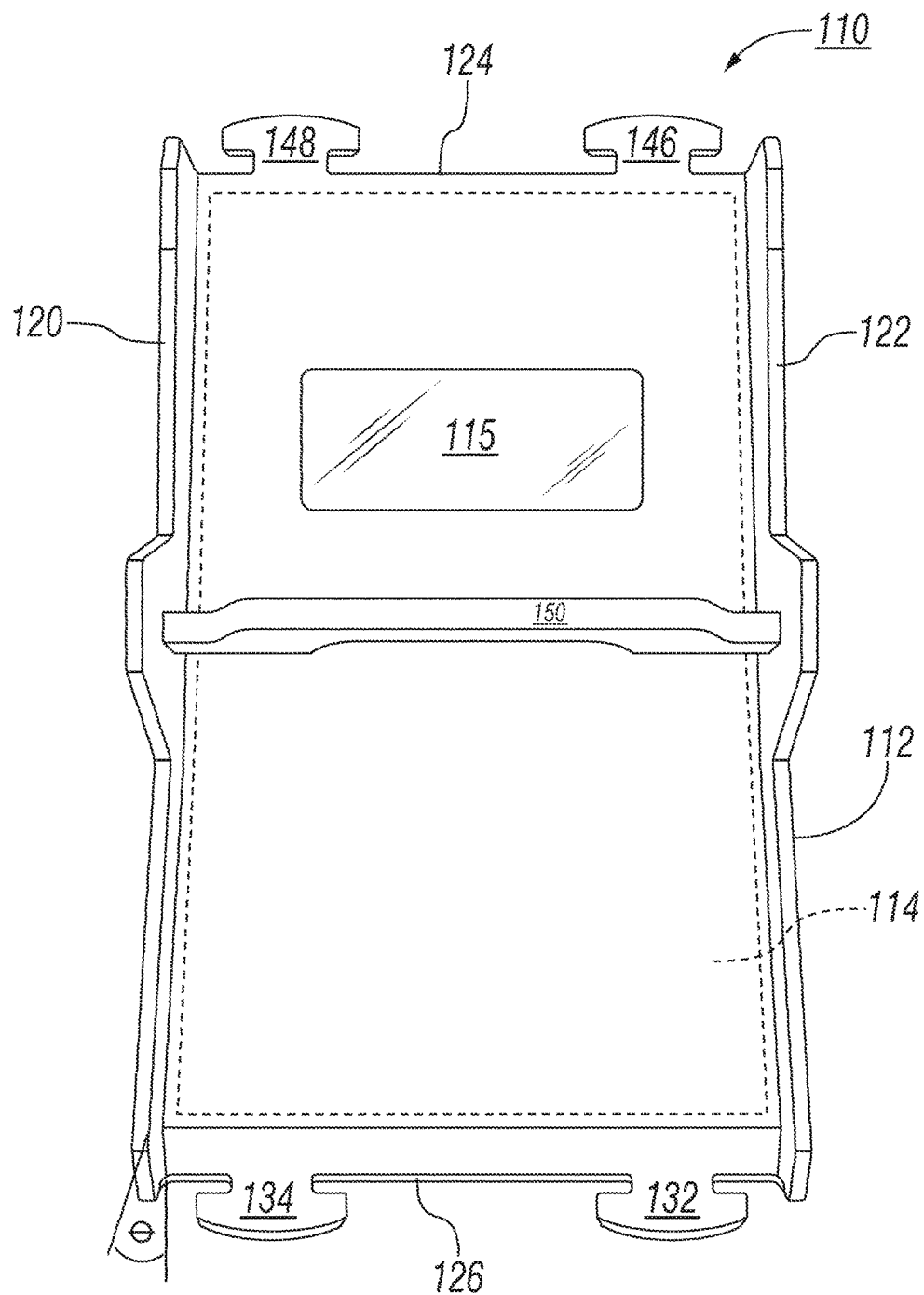
FIG. 12 is an elevational view of a shield according to another aspect of the disclosure.

In the embodiment shown in FIG. 12, a radiation blocking system is designated in general by the number 110. The system 110 is designed to permit a doctor or technician to remain in an X-Ray examination room near a patient during an X-Ray procedure by reducing radiation exposure to the medical personnel. The system 110 generally includes a frame 112 having a right-side wall 120, a left side wall 122, a top border 124, and a bottom border 126. A radiation shield or barrier 114 is interposed within the frame 112, which may be a durable, reusable material such as HDPE, which will not break down from repeated cleansing with sterile wipes or other sterilization processes. The barrier 114 (shown in phantom for clarity) may include a unitary or insertable sheet of radiation reducing material such as lead, antimony, tin, cadmium, rhodium, barium, bismuth, cesium, tungsten, or any suitable material to block or attenuate radiation. The exemplary barrier 114 may be about 1/16 of an inch or about 1.58 mm in thickness and sufficiently radio-dense to absorb, inhibit, attenuate, or block ionizing radiation emanating from an x-ray or associated scatter radiation.

As FIG. 12 further shows, the frame 112 along with its integral radiation shield 114 may be connected to a platform (see, e.g., FIG. 2) via connecting devices or components 132, 134, 146, 148, although other attachment mechanisms such as snaps or the like may be used in the alternative or in addition to components 132, 134, 146, 148.

FIG. 12 also shows that the radiation shield 114 may substantially perpendicular or vertical relative to an examination table if straight tabs or components 146, 148 are inserted in a holding platform or attached to an examination table. Alternatively, if the frame 112 is inverted, the tabs 132, 134, which are angled in this example to some degree θ, e.g., 25 degrees (25°), will cause the frame 112 to extend or incline to some degree over the table to allow medical personnel to reach around the frame 112 in a direction of a patient. Because the lead-lined assembly 110 can weigh as much as ten pounds (10 lbs.), a handle 150 can be provided to help with lifting and positioning the assembly 110. Still further, FIG. 12 shows that a viewing window 115 may be provided in the assembly 110. The window 115 is transparent and is a lead-acrylic sheet between about 8 mm to about 24 mm in thickness, particularly about 12 mm thick. The 12 mm lead-acrylic sheet provides radiation protection equivalent to a lead sheet having a thickness of 0.5 mm.

Figure 13:
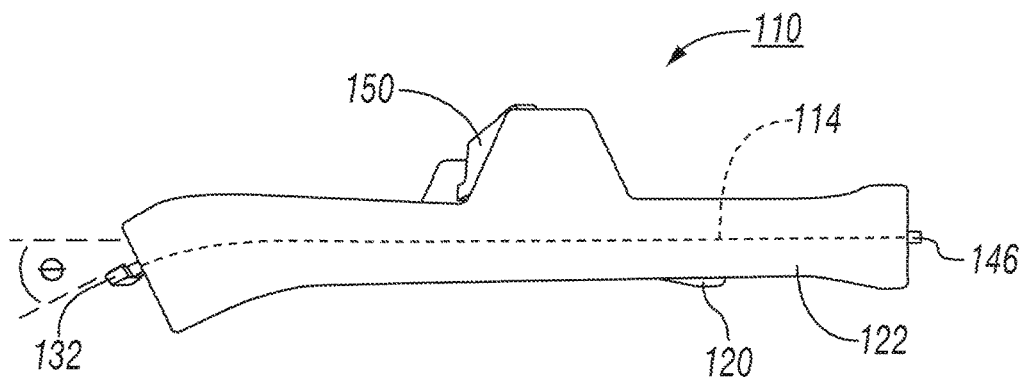
FIG. 13 is a side view of the shield as in FIG. 12, particularly showing a radiation attenuating aspect of the shield in phantom.

FIG. 13 shows the radiation shield 114 of FIG. 12 in phantom running substantially from the tab 146 end to the tab 132 end of the assembly 110. As noted above, by inserting the angled tab 132 into an examination table, the assembly 110 will incline over the table to some degree θ, e.g., 25 degrees (25°), to allow medical personnel to reach around the assembly 110 in a direction of a patient. The handle 150 introduced above is provided in this example to assist personnel with lifting and positioning the assembly 110.

Figure 14:
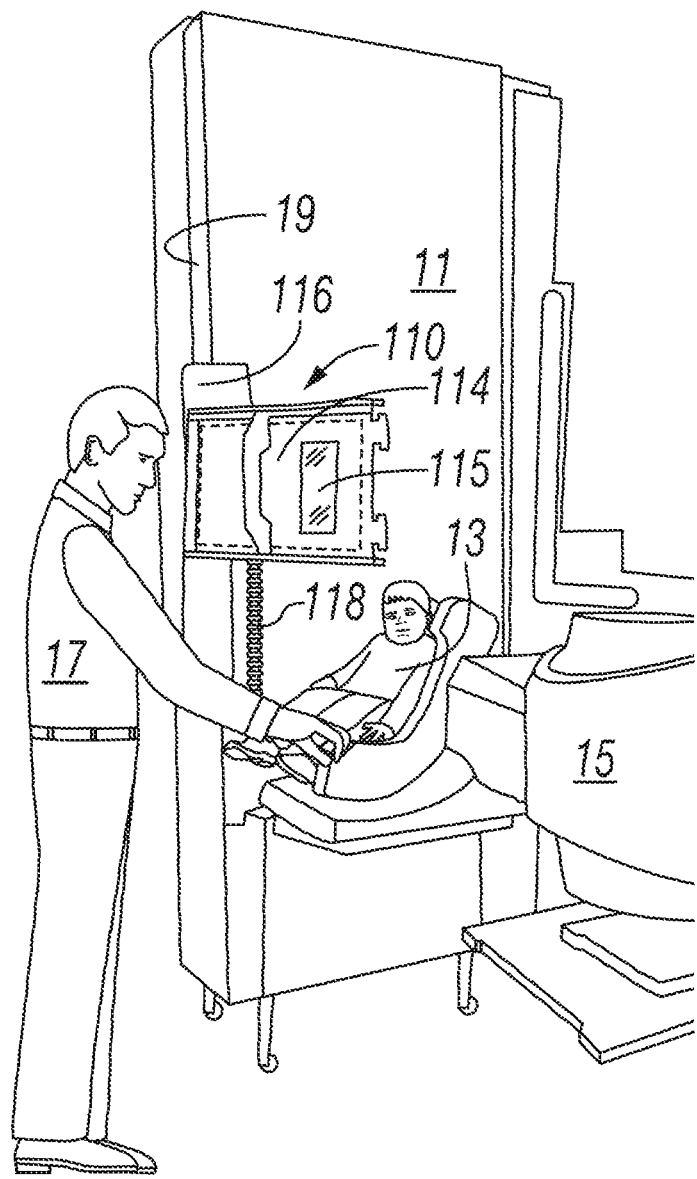
FIG. 14 is a perspective view of the shield as in FIG. 12, particularly showing a different orientation of the shield according to an aspect of the disclosure.

Turning now to FIG. 14 an examination table 11 is rotated substantially perpendicular or vertical relative to ground. Here, the assembly 110 with imbedded radiation shield 114 is attached to a base 116, which in turn is attached to an attachment assembly 118 that is connected to an edge 19 of the table 11. Due to the T-shaped tabs 132, 134 (see FIG. 12) the assembly 110 remains fixed relative to the table 11 no matter which direction the table 11 is rotated. Also in this example, the angled tabs 132, 134 (see FIG. 12) cause the assembly 110 to incline over the table 11 to allow medical personnel 17 to reach around the assembly 110 in a direction of an infant patient 13 while undergoing X-Ray irradiation from an X-ray machine 15. Here, the medical personnel 17 can remain behind the viewing window 115 to monitor the infant patient 13 while simultaneously holding the patient 13 steady, for example.

Figure 15:
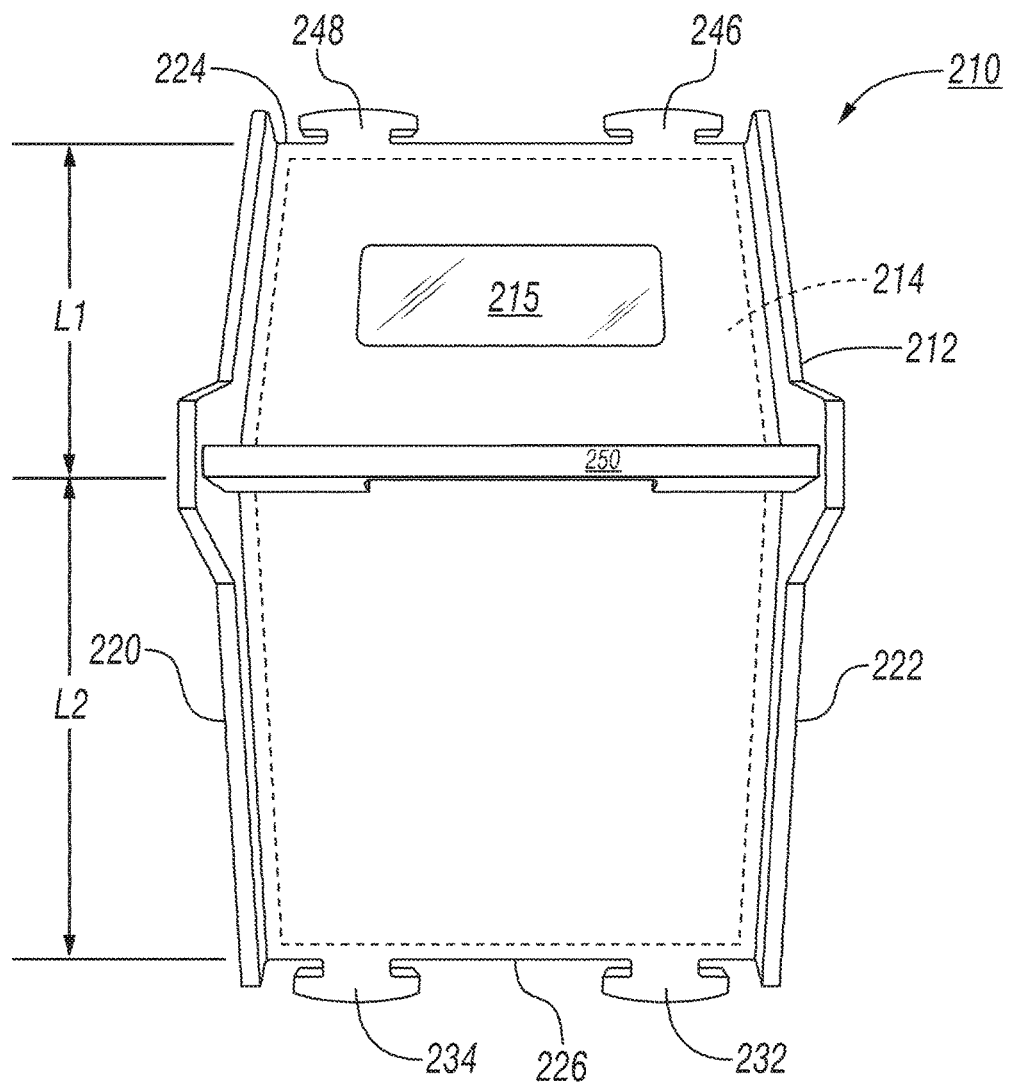
FIG. 15 is another embodiment of a shield according to a further aspect of the disclosure.

FIG. 15 shows another embodiment in which a radiation blocking system is designated in general by the number 210. The system 210 permits attending medical personnel to remain in an X-Ray examination room near a patient during an X-Ray procedure by reducing radiation exposure to the medical personnel. The system 210 generally includes a frame 212 having a left side wall 220, a right-side wall 222, a top border 224, and a bottom border 226. A radiation shield or barrier 214 is interposed within the frame 212, which may be a durable, reusable material such as HDPE that will not break down from repeated cleansing with sterile wipes or other sterilization processes. The barrier 214 (shown in phantom for clarity) may include a unitary or insertable radiation reducing material such as lead, antimony, tin, cadmium, rhodium, barium, bismuth, cesium, tungsten, or any suitable material to block or attenuate radiation. The exemplary barrier 214 may be about 1/16 of an inch or about 1.58 mm in thickness and sufficiently radio-dense to absorb, inhibit, attenuate, or block ionizing radiation emanating from an x-ray or associated scatter radiation.

FIG. 15 further shows that the frame 212 includes multiple tabs or attachment components 232, 234, 246, 248. Either tabs 232, 234 or tabs 246, 248 can be inserted in a base or holding platform or attached to an examination table. However, a length L1 measured from a handle 250 to end 224 may differ from a length L2 measured from the handle 250 to end 226. In this example, L1 is approximately 25.5 centimeters (cm) and L2 is approximately 29.5 cm in length. Thus, due to curvature proximate the handle 250, by inverting the frame 212 and using either tabs 232, 234 or tabs 246, 248 to connect to the examination table, the height of the system 210 can be adjusted, for instance, to accommodate medical personnel of different height.

FIG. 15 also shows a radio-dense viewing window 215, which medical personnel can remain behind to monitor a patient. The window 215 is a transparent, lead-acrylic sheet between about 8 mm to about 24 mm in thickness, particularly about 12 mm thick. The 12 mm lead-acrylic sheet provides radiation protection equivalent to a lead sheet having a thickness of 0.5 mm. Although only one window 215 is shown on side L1, another radio-dense viewing window could be provided on side L2.

Figure 16:
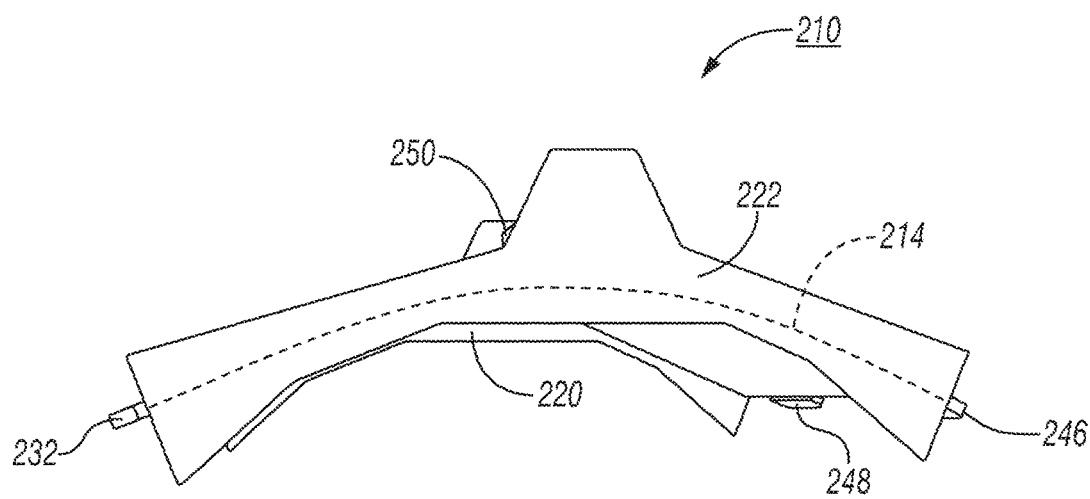
FIG. 16 is a side view of the shield as in FIG. 15, particularly showing a radiation attenuating aspect of the shield in phantom.

FIG. 16 shows the radiation shield 214 of FIG. 15 in phantom running substantially from the tab 246 end to the tab 232 end of the assembly 210. As noted above, due to the off-center bend near the handle 250 that creates L1, L2 (see FIG. 15) by inserting either the end with tab 232 or the end with tab 246 into the examination table or connection device thereon, the assembly 210 will assume a different height. In either case the assembly 210 will incline over the table to some degree θ, e.g., 25 degrees, to allow medical personnel to lean in toward a patient and reach around the assembly 210 if necessary in a direction of the patient.

Figure 17:
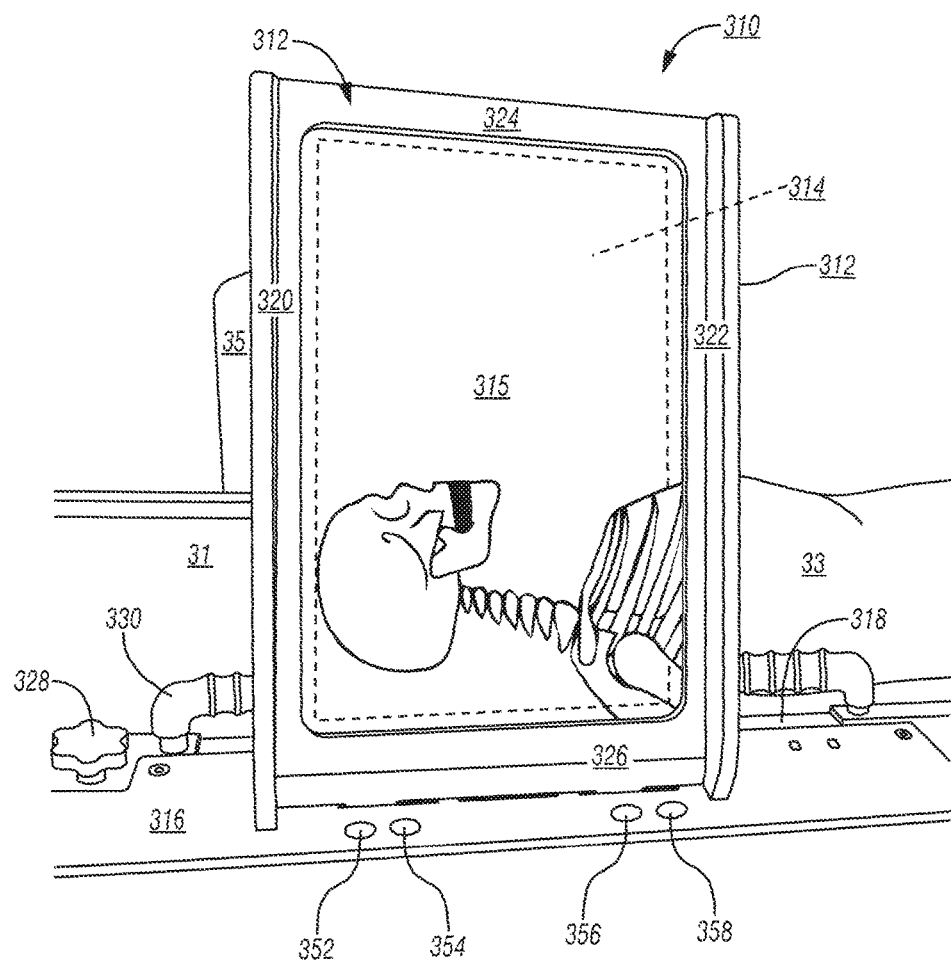
FIG. 17 is a further embodiment of a shield according to the disclosure, particularly showing an integrated monitor in a viewing screen according to another aspect of the disclosure.

Another embodiment is shown in FIG. 17 in which a radiation attenuating and monitoring system 310 broadly includes a holder or frame 312, a radio-dense shield 314, a computer display or monitor 315, and a base or platform 316. The frame 312 attaches to the base 316, which in turn attaches to a connection or attachment device 318 that utilizes, for example, a connector 328 such as a screw-in handle or knob that can be loosened or tightened to attach, adjust, or detach the attachment device 318 from the table 1. Here, the attachment device 318 attaches to an examination table 31 and may also include a handle or grip 330 that can be used to transport or adjust the attachment device 318, or a patient 33 can grip it for support.

More specifically, the frame 312 of FIG. 17 includes a first wall or side 320, a second wall or side 322, a first edge or top 324, and a second edge or bottom 326, which hold the shield 314 and monitor 315 therebetween. Here, a portion of an X-Ray device 35 can be seen which irradiates the patient 33 and is in communication with the monitor 315 to display X-ray results thereon in real time. Medical personnel (not shown) that stand in the foreground of FIG. 17 are protected from radiation being emitted from the X-Ray machine 35.

FIG. 17 also shows that the system 310 may include a series of controls. For instance, a power or on-button 352 may be used to activate the monitor 315 as well as a camera (described in FIG. 18 below). An off-button 354 is provided to power off the system 310. Still further, a camera zoom control 356 and a record button 358 for both audio and visual may be provided.

Figure 18:
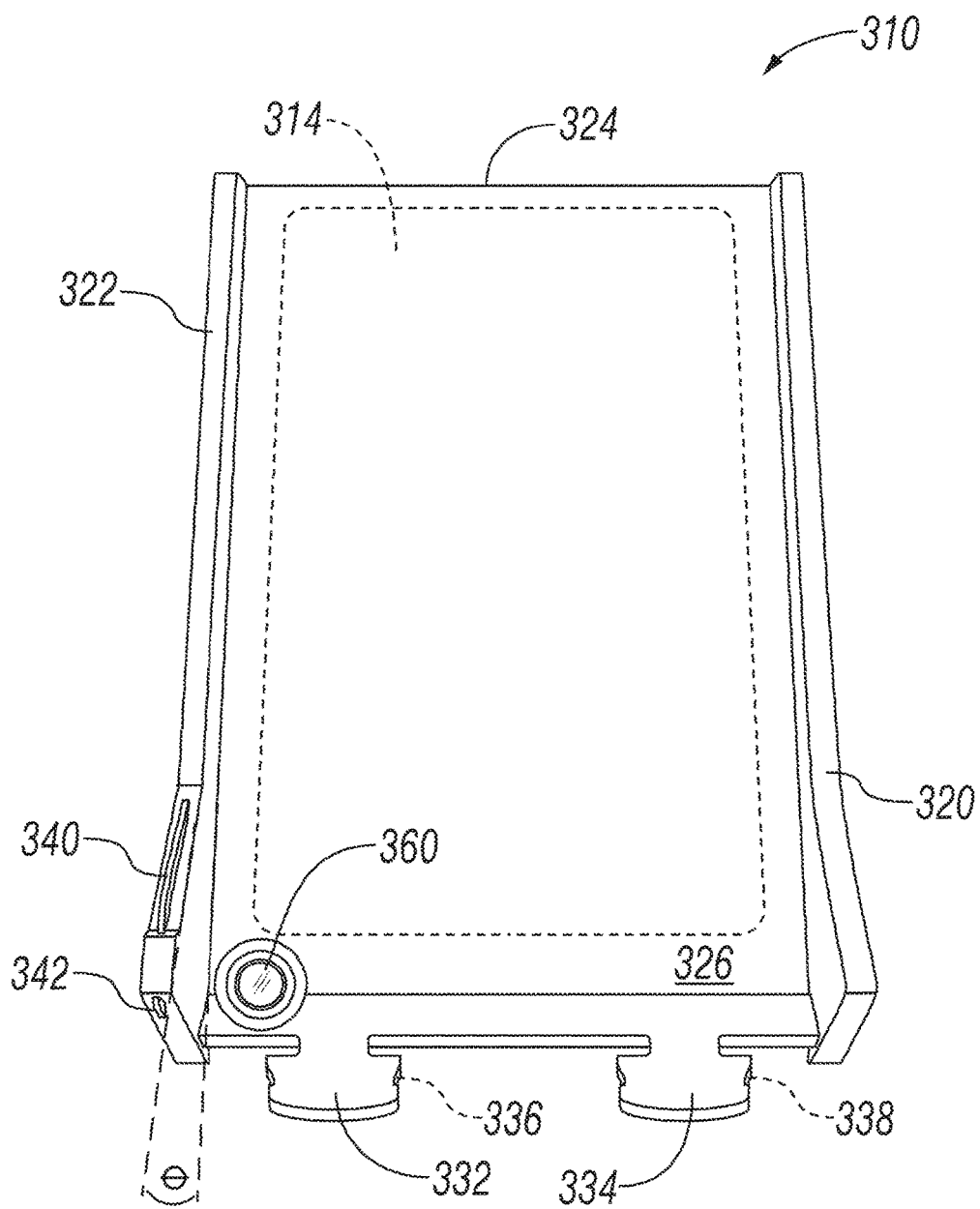
FIG. 18 is a rear elevational view of the shield as in FIG. 17, particularly showing a recording device according to another aspect of the disclosure.

FIG. 18 shows the system 310 of FIG. 17 from the examination table side with the first wall 320, the second wall 322, the top 324, and the bottom 326. Tabs 332, 334 with indentations 336, 338 extend at an angle from the bottom 326 to cause the system 310 to tilt at a desired degree θ, usually in a direction of the examination table. Here also, a camera 360 is provided, which is activated by the on-button 352 and controlled by the zoom and record controls 356, 358 (see FIG. 17). Also shown, release control 340 and pin 342 serve to lock the system 310 in place during an examination.

Figure 19:
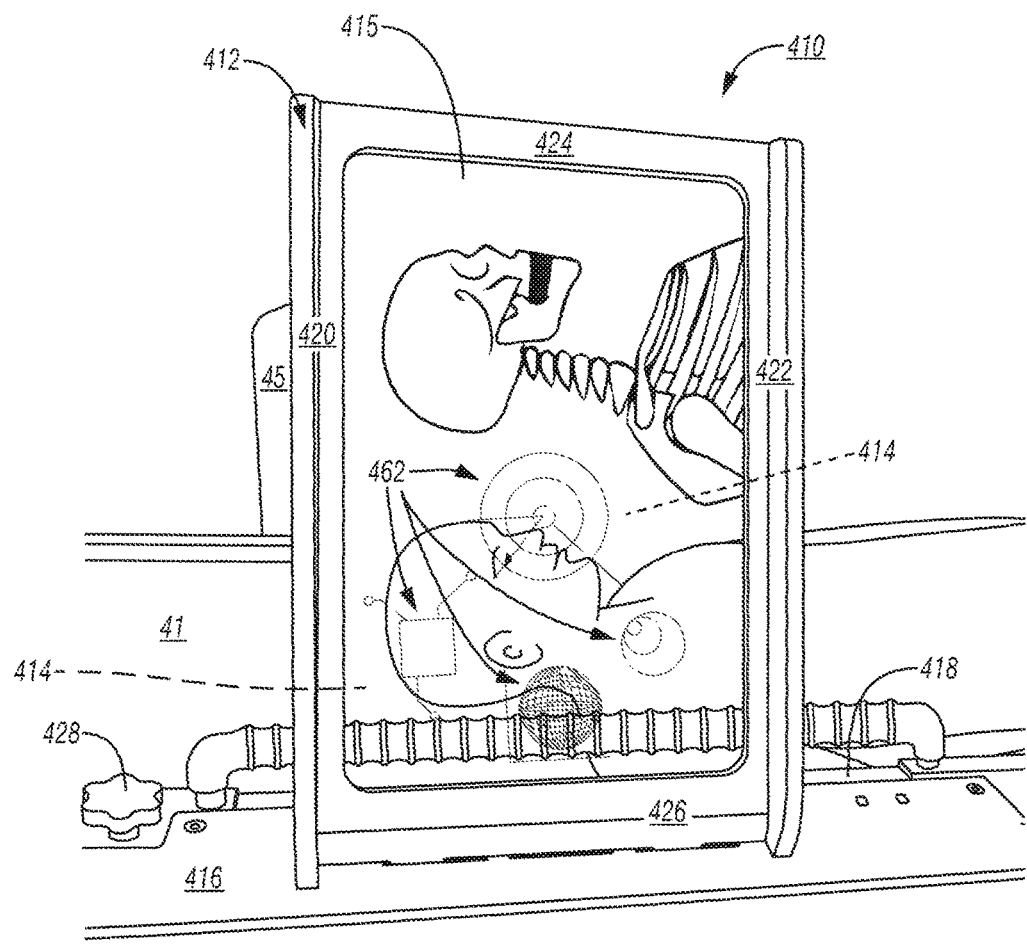
FIG. 19 is a perspective view of a shield according to another embodiment of the disclosure, particularly showing a split screen with monitor and partially transparent touch screen according to another aspect of the disclosure.

FIG. 19 shows another embodiment in which a radiation attenuating screen and monitoring system 410 broadly includes a holder or frame 412, a radio-dense screen 414, an X-Ray viewing monitor 415, and a base or platform 416.

The frame 412 has a first wall 420, a second wall 422, a top 424, and a bottom 426, which attaches to a base 416 that in turn connects to an attachment device 418 that utilizes, for example, a connector 428 such as a screw-in handle or knob that can be loosened or tightened to attach, adjust, or detach the attachment device 418 from the table 41. Here, the attachment device 418 attaches to an examination table 41 and may also include a handle or grip 430 that can be used to transport or adjust the attachment device 418 with its attached base 416.

In the embodiment of FIG. 19, the bottom screen 414 is a transparent, lead-acrylic sheet from between about 8 mm to about 24 mm in thickness, particularly about 12 mm thick. The screen 414 allows medical personnel to remain safely in the examination room during irradiation in order to conduct ancillary procedures during an X-ray. Further, the exemplary screen 414 includes touch sensitive icons 462 to turn on the monitor 415 and/or a camera on its table side (see, e.g., FIG. 18), to zoom in on an X-Ray in real time showing on the top monitor 415 and to record audio and visual data during the examination.

Experimental Results

Introduction.

On about Jun. 29, 2016, a testing service conducted a radiation survey in an X-ray examination room on a prototype based on the embodiments of the present disclosure; i.e., an angled radiation shield designed to allow a technologist to remain in the examination room near a patient during an X-ray procedure to reduce radiation exposure to the technologist even while inclining toward the patient to make contemporaneous adjustments to the patient or to conduct related procedures during the X-ray procedure. The purpose of the survey was to determine the percentage and effectiveness of the prototype to reduce radiation levels to medical staff.

Equipment and Set-Up.

An X-ray unit was set at 75 kVp, 4.5 mA, pulse UN, 15 fps. The shield was attached to an X-ray examination table.

Measurements and Test Results.

Two radiation measurements were taken without the shield and two were taken with the shield in place. As shown in Table 1 below, measurement #1 was made near the top of the shield approximately where the technologist's face would be. See, e.g., FIG. 1. Measurement #2 was made near the bottom of the shield where the technologist abdomen would be. Id. The measurements were made closer to the patient than previous measurements as the technologist would most likely be leaning toward the patient. Distance was approximately four to six inches from the surface of the shield. See, e.g., FIG. 1 wherein the technologist is leaning toward the screen and the patient at approximately 25 degrees and reaching around the shield to adjust the patient.

TABLE 1

| Measurement | Without Shield | Shield in place |
| --- | --- | --- |
| 1 | 1000 mR/hr | 62 mR/hr |
| 2 | 400 mR/hr | 10.5 mR/hr |

The test results indicated an overall exposure rate reduction to the technologist by about 95%. More specifically, radiation reduction to the technologist at eye level was by about ninety percent (90%) to about ninety-five percent (95%), more particularly, by about ninety-three point eight percent (93.8%), and at a level of the abdomen: by about ninety-five percent (95%) to about ninety-nine percent (99%), more particularly, by about ninety-seven point four percent (97.4%). In short, radiation reduction exposure to attending staff may be reduced by between about 90% to about 99% percent over a system that lacks the radiation attenuating and angular features described herein. Significantly reduced radiation exposure to procedure staff not only protects these professionals from unnecessary radiation, but such reductions increase their procedure room longevity based on parameters mandated by federal and state radiation exposure limits.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

EMBODIMENTS

Exemplary embodiments may include:

Embodiment 1

A radiation shield assembly, comprising:
a radiation attenuating screen being at least partially transparent;
a base attachable substantially parallel to a surface of an examination table, the radiation attenuating screen connectable to the base to interpose the radiation attenuating screen between attending medical staff and a patient disposed on the examination table, the partially transparent radiation attenuating screen configured to permit the medical staff to manipulate control icons on the radiation attenuating screen while simultaneously viewing the patient therethrough;
wherein the radiation attenuating screen depends at an angle from the base in a direction of the surface of the examination table to permit the medical staff to incline in a direction of the patient, the radiation attenuating screen including a radiodense material to reduce radiation exposure to the medical staff while irradiating the patient.

Embodiment 2

The assembly as in embodiment 1, wherein the radiation attenuated while irradiating the patient is measured in milliroentgens per hour (mR/hr).

Embodiment 3

The assembly as in any one of embodiments 1-2, wherein the radiation attenuating screen is a lead (Pb) acrylic sheet from about 10 mm to about 14 mm in thickness, more particularly about 12 mm.

Embodiment 4

The assembly as in any one of embodiments 1-3, wherein the radiation attenuating screen includes a touch screen, the control icons being selected from the group consisting of an on-control, an off-control, a camera record control, a zoom control, a voice control and combinations thereof.

Embodiment 5

The assembly as in any one of embodiments 1-4, wherein the radiation attenuating screen reduces radiation exposure to facial areas of attending medical staff from about ninety percent to about ninety-four percent, more particularly by about ninety-three point eight percent (93.8%).

Embodiment 6

The assembly as in any one of embodiments 1-5, wherein the radiation attenuating screen reduces radiation exposure to abdominal areas of attending medical staff from about ninety-five percent to about ninety-nine percent, more particularly by about ninety-seven point four percent (97.4%)

Embodiment 7

The assembly as in any one of embodiments 1-6, wherein the angle of the radiation attenuating screen is about twenty-five degrees measured from vertical.

Embodiment 8

The assembly as in any one of embodiments 1-7, wherein the angle of the radiation attenuating screen is adjustable from about five degrees to about forty-five degrees measured from vertical.

Embodiment 9

The assembly as in any one of embodiments 1-8, further comprising a frame disposed about the radiation attenuating screen.

Embodiment 10

The assembly as in embodiment 9, wherein the frame is configured at about twenty-five degrees from vertical to cause the radiation attenuating screen to depend from the base at the angle in the direction of the surface of the examination table.

Embodiment 11

The assembly as in embodiments 9-10, wherein the base includes a plurality of apertures therein and the frame includes a plurality of tabs depending therefrom, the tabs being configured to slot into the apertures to seat the base and the frame together.

Embodiment 12

The assembly as in embodiment 11, wherein the apertures are greater in number than the tabs, the tabs being seated in different apertures to move the radiation attenuating screen relative to the examination table.

Embodiment 13

The assembly as in embodiments 9-12, wherein the frame further comprises a latch retractor and a latch, and the base further comprises a notch to receive the latch, the latch being controllable by the latch retractor to release the latch from the notch.

Embodiment 14

The assembly as in any one of the foregoing embodiments, further comprising an attachment assembly connectable to the examination table, the base being connectable to the attachment assembly.

Embodiment 15

A radiation shield assembly, comprising:
a radiation attenuating shield having a plurality of tabs depending therefrom;
a base attachable substantially parallel to a surface of an examination table, the base having a plurality of apertures therein for receiving the tabs of the radiation attenuating shield to interpose the radiation attenuating shield between attending medical staff and a patient disposed on the examination table, the radiation attenuating shield depending at an angle from the base in a direction of the surface of the examination table to permit the medical staff to incline in a direction of the patient, the radiation attenuating shield including a radiodense material to reduce radiation exposure to the medical staff while irradiating the patient.

Embodiment 16

The assembly as in embodiment 15, wherein the radiation attenuating shield has a top, a bottom, a first side and a second side, and at least two of the tabs extend from the top and at least two tabs extend from the bottom.

Embodiment 17

The assembly as in embodiment 16, wherein at least one set of the tabs at the top and the bottom are inclined to cause the radiation shield assembly to angle toward the table.

Embodiment 18

The assembly as in any one of embodiments 15-17, wherein the radiation shield assembly is formed with a bend to cause the radiation shield assembly to angle toward the table from about five degrees to about forty-five degrees from vertical, more particularly about twenty-five degrees from vertical in a direction of the examination table.

Embodiment 19

The assembly as in embodiment 18, wherein the bend is off center and the radiation shield assembly has a first portion depending from the bend that is longer than a second portion depending from the bend.

Embodiment 20

The assembly as in any one of embodiments 15-18, wherein the radiodense material is equivalent to about 0.5 mm lead.

Embodiment 21

The assembly as in any one of embodiments 15-20, wherein the radiation attenuating screen reduces radiation exposure to attending medical staff from about ninety percent to about ninety-nine percent.

Embodiment 22

A radiation shield assembly, comprising:
a frame having a top, a bottom, a first side and a second side, a plurality of tabs depending from one of the top, bottom, first side or second side;
a radiation attenuating screen disposed within the frame, the radiation attenuating screen being transparent and including a radiodense material to reduce radiation exposure to attending medical staff during a procedure;
a base attachable substantially parallel to a surface of an examination table, the tabs of the frame connectable to the base to interpose the radiation attenuating screen between the attending medical staff and a patient disposed on the examination table, the transparent radiation attenuating screen configured to permit the medical staff to view the patient during the procedure;
wherein the tabs or the frame depend at an angle in a direction of the surface of the examination table to permit the medical staff to incline in a direction of the patient.

Embodiment 23

The assembly as in embodiment 22, wherein the radiation attenuating screen includes a lead (Pb) acrylic sheet from about 10 mm to about 14 mm in thickness, more particularly about 12 mm.

Embodiment 24

The assembly as in any one of embodiments 22-23, wherein the radiation attenuating screen reduces radiation exposure to attending medical staff from about ninety percent to about ninety-nine percent.

Embodiment 25

The assembly as in any one of embodiments 22-24, further comprising controls connected to one of the frame or the base, the controls being selected from the group consisting of an on-control, an off-control, a camera record control, a zoom control, a voice control and combinations thereof.

Embodiment 26

The assembly as in any one of embodiments 22-25, further comprising a camera attachable to the frame, and a portion of the radiation attenuating screen is a video monitor in communication with the camera for monitoring the patient.

Embodiment 27

The assembly as in any one of embodiments 22-26, wherein the angle of the radiation attenuating screen is adjustable from about five degrees to about forty-five degrees from vertical, more particularly about twenty-five degrees from vertical in a direction of the examination table.

That which is claimed is:
1. A radiation shield assembly, comprising:
  a radiation attenuating touch screen being at least partially transparent to visible light;

a base attachable substantially parallel to a surface of an examination table, the radiation attenuating touch screen connectable to the base to interpose the radiation attenuating touch screen between attending medical staff and a patient disposed on the examination table, the partially transparent radiation attenuating touch screen configured to permit the medical staff to manipulate control icons on the radiation attenuating touch screen while simultaneously viewing the patient therethrough; and wherein the radiation attenuating touch screen depends at an angle from the base in a direction of the surface of the examination table to permit the medical staff to incline in a direction of the patient, the radiation attenuating touch screen including a radiodense material to reduce radiation exposure to the medical staff while irradiating the patient.

2. The radiation shield assembly as in claim 1, wherein the radiation attenuated while irradiating the patient is measured in milliroentgens per hour (mR/hr).

3. The radiation shield assembly as in claim 1, wherein the radiation attenuating touch screen is a lead (Pb) acrylic sheet from about 10 mm to about 14 mm in thickness, more particularly about 12 mm.

4. The radiation shield assembly as in claim 1, wherein the radiation attenuating touch screen includes control icons being selected from the group consisting of an on-control, an off-control, a camera record control, a zoom control, a voice control and combinations thereof.

5. The radiation shield assembly as in claim 1, wherein the radiation attenuating touch screen reduces radiation exposure to facial areas of attending medical staff from about ninety percent to about ninety-four percent, more particularly by about ninety-three point eight percent (93.8%).

6. The radiation shield assembly as in claim 1, wherein the radiation attenuating touch screen reduces radiation exposure to abdominal areas of attending medical staff from about ninety-five percent to about ninety-nine percent, more particularly by about ninety-seven point four percent (97.4%).

7. The radiation shield assembly as in claim 1, wherein the angle of the radiation attenuating touch screen is about twenty-five degrees measured from vertical.

8. The radiation shield assembly as in claim 1, wherein the angle of the radiation attenuating touch screen is adjustable from about five degrees to about forty-five degrees measured from vertical.

9. The radiation shield assembly as in claim 1, further comprising a frame disposed about the radiation attenuating touch screen.

10. The radiation shield assembly as in claim 9, wherein the frame is configured at about twenty-five degrees from vertical to cause the radiation attenuating touch screen to depend from the base at the angle in the direction of the surface of the examination table.

11. The radiation shield assembly as in claim 9, wherein the base includes a plurality of apertures therein and the frame includes a plurality of tabs depending therefrom, the tabs being configured to slot into the apertures to seat the base and the frame together.

12. The radiation shield assembly as in claim 11, wherein the apertures are greater in number than the tabs, the tabs being seated in different apertures to move the radiation attenuating touch screen relative to the examination table.

13. The radiation shield assembly as in claim 9, wherein the frame further comprises a latch retractor and a latch, and the base further comprises a notch to receive the latch, the latch being controllable by the latch retractor to release the latch from the notch.

14. The radiation shield assembly as in claim 1, further comprising an attachment assembly connectable to the examination table, the base being connectable to the attachment assembly.

15. A radiation shield assembly, comprising:
a radiation attenuating shield having a plurality of tabs depending therefrom and including a touch screen being at least partially transparent to visible light configured to permit the medical staff to manipulate control icons on the touch screen while simultaneously viewing the patient therethrough; and
a base attachable substantially parallel to a surface of an examination table, the base having a plurality of apertures therein for receiving the tabs of the radiation attenuating shield to interpose the radiation attenuating shield between attending medical staff and a patient disposed on the examination table, the radiation attenuating shield depending at an angle from the base in a direction of the surface of the examination table to permit the medical staff to incline in a direction of the patient, the radiation attenuating shield including a radiodense material to reduce radiation exposure to the medical staff while irradiating the patient.

16. The radiation shield assembly as in claim 15, wherein the radiation attenuating shield has a top, a bottom, a first side and a second side, and at least two of the tabs extend from the top and at least two tabs extend from the bottom.

17. The radiation shield assembly as in claim 16, wherein at least one set of the tabs at the top and the bottom are inclined to cause the radiation shield assembly to angle toward the table.

18. The radiation shield assembly as in claim 15, wherein the radiation shield assembly is formed with a bend to cause the radiation shield assembly to angle toward the table from about five degrees to about forty-five degrees from vertical, more particularly about twenty-five degrees from vertical in a direction of the examination table.

19. The radiation shield assembly as in claim 18, wherein the bend is off center and the radiation shield assembly has a first portion depending from the bend that is longer than a second portion depending from the bend.

20. The radiation shield assembly as in claim 15, wherein the radiodense material is equivalent to about 0.5 mm lead.

21. The radiation shield assembly as in claim 15, wherein the radiation attenuating screen reduces radiation exposure to attending medical staff from about ninety percent to about ninety-nine percent.

22. A radiation shield assembly, comprising:
a frame having a top, a bottom, a first side and a second side, a plurality of tabs depending from one of the top, bottom, first side or second side;
a radiation attenuating touch screen disposed within the frame, the radiation attenuating touch screen being transparent to visible light configured to permit the medical staff to manipulate control icons on the radiation attenuating touch screen while simultaneously viewing the patient therethrough and including a radiodense material to reduce radiation exposure to attending medical staff during a procedure; and
a base attachable substantially parallel to a surface of an examination table, the tabs of the frame connectable to the base to interpose the radiation attenuating touch screen between the attending medical staff and a patient disposed on the examination table, the transparent radiation attenuating touch screen configured to permit the medical staff to view the patient during the procedure;

wherein the tabs or the frame depend at an angle in a direction of the surface of the examination table to permit the medical staff to incline in a direction of the patient.

23. The radiation shield assembly as in claim 22, wherein the radiation attenuating touch screen includes a lead (Pb) acrylic sheet from about 10 mm to about 14 mm in thickness, more particularly about 12 mm.

24. The radiation shield assembly as in claim 22, wherein the radiation attenuating touch screen reduces radiation exposure to attending medical staff from about ninety percent to about ninety-nine percent.

25. The radiation shield assembly as in claim 22, further comprising controls connected to one of the frame or the base, the controls being selected from the group consisting of an on-control, an off-control, a camera record control, a zoom control, a voice control and combinations thereof.

26. The radiation shield assembly as in claim 22, further comprising a camera attachable to the frame, and a portion of the radiation attenuating touch screen is a video monitor in communication with the camera for monitoring the patient.

27. The radiation shield assembly as in claim 22, wherein the angle of the radiation attenuating touch screen is adjustable from about five degrees to about forty-five degrees from vertical, more particularly about twenty-five degrees from vertical in a direction of the examination table.

* * * * *